(12) United States Patent
Dutertre et al.

(10) Patent No.: US 11,389,181 B2
(45) Date of Patent: Jul. 19, 2022

(54) STEERABLE SYSTEMS AND METHODS FOR ACCESSING BONE

(71) Applicant: Stryker European Operations Limited, Carrigtwohill (IE)

(72) Inventors: Guillaume Dutertre, Paris (FR); Jean-Baptiste Zerlauth, La Sage (CH); Jean-Francois Oglaza, Balma (FR); Yves-Alain Ratron, Grenoble (FR)

(73) Assignee: Stryker European Operations Limited, Carrigtwohill (IE)

( * ) Notice: Subject to any disclaimer, the term of this patent is extended or adjusted under 35 U.S.C. 154(b) by 228 days.

(21) Appl. No.: 16/882,902

(22) Filed: May 26, 2020

(65) Prior Publication Data
US 2020/0281609 A1 Sep. 10, 2020

Related U.S. Application Data

(63) Continuation of application No. 15/760,455, filed as application No. PCT/EP2016/071922 on Sep. 16, 2016, now Pat. No. 10,660,659.

(30) Foreign Application Priority Data

Sep. 16, 2015 (FR) ...................................... 1558697

(51) Int. Cl.
*A61B 17/16* (2006.01)
*A61B 17/88* (2006.01)

(52) U.S. Cl.
CPC ...... *A61B 17/1671* (2013.01); *A61B 17/1642* (2013.01); *A61B 17/8805* (2013.01); *A61B 17/8811* (2013.01)

(58) Field of Classification Search
CPC . A61B 17/16; A61B 17/1637; A61B 17/1642; A61B 17/1662; A61B 17/1671;
(Continued)

(56) References Cited

U.S. PATENT DOCUMENTS 8,419,730 B2 * 4/2013 Pellegrino .......... A61B 18/1487
606/41
9,480,485 B2 * 11/2016 Aho .................. A61B 17/1631
(Continued)

FOREIGN PATENT DOCUMENTS

WO 0033909 A1 6/2000
WO 2014093464 A1 6/2014

OTHER PUBLICATIONS

French Preliminary Search Report for Application No. FR1558697 dated Mar. 23, 2016.
(Continued)

*Primary Examiner* — Eric S Gibson
(74) *Attorney, Agent, or Firm* — Howard & Howard Attorneys PLLC

(57) ABSTRACT

A steerable system and methods for accessing bone. A control mechanism includes a handle configured to be detachably secured to a trocar. The handle includes a drive shaft coupled to a sliding shaft such that relative rotation is prevented and relative translation is permitted. A rod having a preformed bend is removably disposed within the cannula. The rod is prevented from rotating relative to the drive shaft such that a deflection plane of the preformed bend is predefined relative to each of the sliding shaft, the handle, and the trocar when the handle is coupled to the trocar. Rotating a sliding ring of the handle translates the drive shaft to advance the rod beyond the trocar such that the preformed bend extends laterally out of the trocar in the deflection plane. The rod may be removed from the cannula, and material may be injected through the cannula.

20 Claims, 12 Drawing Sheets

(58) Field of Classification Search
CPC . A61B 17/88; A61B 17/8802; A61B 17/8805; A61B 17/8811; A61B 17/8816; A61B 17/8819
See application file for complete search history.

(56) References Cited

U.S. PATENT DOCUMENTS

| | | | | |
|---|---|---|---|---|
| 9,724,107 | B2* | 8/2017 | Pellegrino | A61B 17/3403 |
| 10,660,659 | B2* | 5/2020 | Dutertre | A61B 17/8811 |
| 2006/0089609 | A1* | 4/2006 | Bleich | A61B 17/320758 |
| | | | | 604/272 |
| 2008/0065116 | A1* | 3/2008 | Lee | A61B 17/2909 |
| | | | | 606/208 |
| 2009/0069842 | A1* | 3/2009 | Lee | A61B 50/30 |
| | | | | 606/205 |
| 2009/0171147 | A1* | 7/2009 | Lee | A61B 17/29 |
| | | | | 600/137 |
| 2009/0326538 | A1* | 12/2009 | Sennett | A61B 17/8855 |
| | | | | 606/86 R |
| 2010/0094269 | A1* | 4/2010 | Pellegrino | A61B 18/1815 |
| | | | | 604/500 |
| 2010/0185161 | A1* | 7/2010 | Pellegrino | A61B 17/1642 |
| | | | | 604/272 |
| 2010/0268234 | A1* | 10/2010 | Aho | A61B 17/1631 |
| | | | | 606/80 |
| 2010/0286782 | A1* | 11/2010 | Schaller | A61B 17/7097 |
| | | | | 623/17.12 |
| 2010/0324506 | A1 | 12/2010 | Pellegrino et al. | |
| 2011/0166575 | A1* | 7/2011 | Assell | A61B 17/1671 |
| | | | | 606/79 |
| 2013/0012951 | A1* | 1/2013 | Linderman | A61B 17/8855 |
| | | | | 606/93 |
| 2013/0110145 | A1* | 5/2013 | Weitzman | A61B 17/1642 |
| | | | | 606/170 |
| 2013/0245533 | A1 | 9/2013 | Kahn et al. | |
| 2014/0276471 | A1 | 9/2014 | Emery et al. | |
| 2015/0182234 | A1* | 7/2015 | Mahoney | A61B 17/1642 |
| | | | | 606/79 |
| 2015/0297246 | A1* | 10/2015 | Patel | A61B 17/3472 |
| | | | | 606/79 |
| 2016/0030060 | A1* | 2/2016 | Tally | A61B 17/1671 |
| | | | | 606/84 |
| 2016/0278791 | A1* | 9/2016 | Pellegrino | A61B 18/148 |
| 2018/0116702 | A1* | 5/2018 | Purdy | A61B 17/8819 |
| 2018/0263648 | A1* | 9/2018 | Dutertre | A61B 17/3472 |
| 2019/0125538 | A1* | 5/2019 | Assell | A61B 17/1671 |
| 2020/0281609 | A1* | 9/2020 | Dutertre | A61B 17/1642 |

OTHER PUBLICATIONS

International Search Report for Application No. PCT/EP2016/071922 dated Dec. 14, 2016.

* cited by examiner

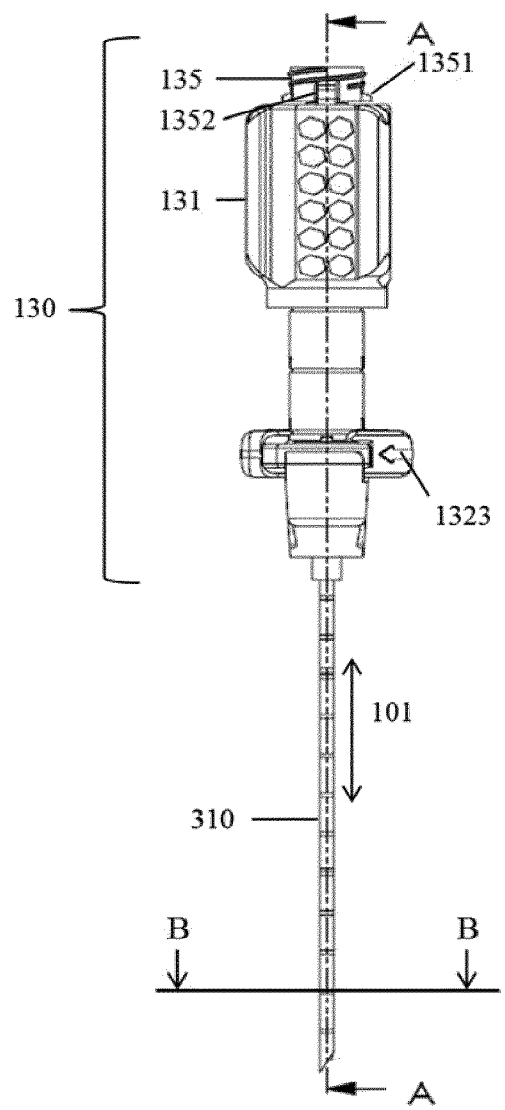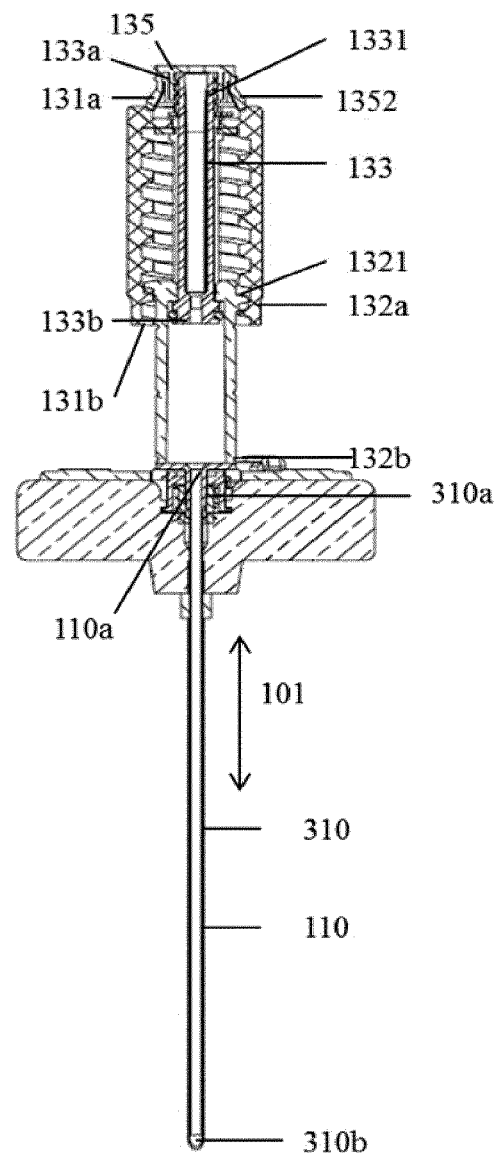
FIG. 16
FIG. 17

STEERABLE SYSTEMS AND METHODS FOR ACCESSING BONE

PRIORITY CLAIM

This is a continuation of U.S. application Ser. No. 15/760,455, filed Mar. 15, 2018, which is a national stage entry of International Application No. PCT/EP2016/071922, filed Sep. 16, 2016, which claims priority to and all the benefits of French Patent Application No. 1558697, filed Sep. 16, 2015, the entire contents of each are hereby incorporated by reference.

FIELD OF THE INVENTION

The present invention pertains to the field of medical devices, in particular orthopedic devices. The invention especially relates to improved mechanisms for controlling a rod used for creating cavities in tissue.

BACKGROUND OF INVENTION

Vertebral compression fractures involve the collapse of one or more vertebral bodies in the spine. Vertebral compression fractures or related spinal deformities may initiate, for instance, from metastatic diseases, injuries or osteoporosis.

Conventional surgery for treating vertebral compression, often referred to as vertebroplasty, includes a cannula or a needle inserted through the posterior of a targeted vertebral body, usually through the pedicles. Once positioned within the compressed vertebral body, bone cement is pushed through the needle into the vertebral body. Variations of vertebroplasty include the deployment of mechanical devices or expansion of a balloon to restore the height of the vertebral body and to create a void in a compressed vertebral body; bone cement is then inserted into the space to stabilize the devices and to strengthen the vertebral body.

In order to sufficiently access a vertebral body for complete infusion of cement it is known to use curved needle enabling interdigitation of the cement.

Such curved needles are often made of shape-memory alloys. For instance, WO 00/33909 discloses a needle assembly comprising a hollow, curved, superelastic infusion needle. The needle assembly comprises an infusion needle made of a superelastic material such as nitinol and an outer cannula for introduction into the body of a patient. The rigid outer cannula is required as the initial access to the vertebral body must be made using a relatively straight approach. Upon deployment from the outer cannula, the needle cannula substantially returns to the preformed curved configuration for the introduction of materials at areas lateral to the entry path of the needle assembly. In order to avoid coring the bone tissue during introduction, a trocar is inserted inside the outer cannula during introduction; once the outer cannula has been directed to the target site, the trocar is removed and the infusion needle is inserted into the outer cannula.

However, with such devices, the friction between the curved needle and the outer cannula prevents easy introduction of the curved needle. As a result, there is a need for device creating voids within tissue with reduced friction during insertion between the curved needle or rod and the outer cannula directed to the target site.

WO2014/093464 discloses a friction reduction covering sized to be received in a cannula and a cavity creation member, biased from a retracted to a deployed configuration, sized to be disposed in the friction reduction covering. With such devices, the curved needle is enclosed within a rigid covering. Consequently, there is reduced friction between the curved needle and the cannula during the surgical procedure. However, within WO2014/093464 the friction reduction covering is not secured to the handle and slides freely in at least one direction.

Therefore there is still of need for improved control of the deployment of the curved needle relative to the handle and/or the friction reduction covering.

SUMMARY

To this end, the present invention relates to a mechanism for controlling rods used for creating cavities in tissue. The control mechanism may further be used for injecting material within said cavity. The present invention also relates to steerable devices for creating cavities and injecting material in tissue, said devices comprising the control mechanism of the invention and the rod.

The present invention thus relates to a control mechanism for controlling a rod having a preformed bent and at least one key, the control mechanism comprising: a handle comprising a sliding ring, a sliding shaft and a drive shaft, each extending along a longitudinal axis and comprising a central opening; wherein the sliding ring is threadedly connected to the sliding shaft; the drive shaft and the sliding shaft are connected by blocking means which prevent axial rotation between the drive shaft and the sliding shaft and which allow the drive shaft to slide within the sliding shaft; and the drive shaft and the sliding ring are connected by connecting means which prevent axial displacement between the drive shaft and the sliding ring and which allow axial rotation between the drive shaft and the sliding ring; and the internal surface of the drive shaft comprises at least one longitudinal groove or keyseat configured to engage the at least one key of the rod; and a friction reduction cannula configured to receive the rod; wherein the friction reduction cannula is secured to the sliding shaft or to the drive shaft.

According to one embodiment, the sliding ring comprises a threaded inner surface and the sliding shaft comprises at least one protrusion protruding outwardly from the sliding shaft and engaging the at least one threaded inner surface of the sliding ring so that axial rotation of the sliding ring causes the sliding shaft to move back and forth along the longitudinal axis.

According to one embodiment, the blocking means comprise at least one key or at least one longitudinal keyseat within the external surface of the drive shaft engaged in respectively at least one longitudinal keyseat or at least one key within the internal surface of the sliding shaft.

According to one embodiment, the connecting means between the drive shaft and the sliding ring comprise a bearing such as a plain bearing.

According to one embodiment, the friction reduction cannula has a longitudinal axis and comprises an opening configured to receive and restrain at least partially the rod, especially the preformed bent, in a straight configuration along the longitudinal axis.

According to one embodiment, the friction reduction cannula is made from steel, preferably stainless steel.

According to one embodiment, the friction reduction cannula comprises a proximal part and a distal part, wherein the distal part is more flexible than the proximal part so that the proximal part restrains the rod in the straight configuration and the distal part does not restrain the rod in the straight configuration.

According to one embodiment, the proximal part of the friction reduction cannula is made from steel, such as stainless steel and a distal part is made from a polymeric material such as polyether block amide.

According to one embodiment, the drive shaft further comprises at its proximal end a connecting thread.

According to one embodiment, the control mechanism further comprising a connecting cap comprising a threaded inner surface assembled onto the connecting thread, said connecting cap comprising a plurality of flexible lugs, protruding distally and outwardly, designed to engage a plurality of openings at or near the proximal end of the sliding ring thereby preventing rotation of the sliding ring.

According to one embodiment, the connecting cap further comprises at least one protrusion or recess, preferably a sawtooth protrusion or a sawtooth recess.

According to one embodiment, the sliding shaft further comprises a hub protruding distally and outwardly.

According to one embodiment, the hub comprises a locking ring designed to secure the sliding shaft with a trocar.

The present invention also relates to a steerable device comprising a control mechanism according to the invention and a rod having a preformed bent and at least one key, the rod being preferably made from a superelastic material, such as an alloy of nickel and titanium.

According to one embodiment, the angle of deflection of the rod ranges from 20° to 150°, preferably from 30° to 130°, more preferably from 40° to 110°.

According to one embodiment, the rod comprises at its proximal end a knob comprising a threaded inner surface designed to be assembled onto the connecting cap, the knob and the rod being connected by means of a bearing which allow axial rotation between the knob and the rod.

According to one embodiment, the knob further comprises at least one protrusion or recess, preferably a sawtooth protrusion or a sawtooth recess designed to be engaged with respectively at least one recess or protrusion of the connecting cap thereby preventing rotation between the connecting cap and the knob.

The present invention also relates to a steerable system comprising a steerable device according to the present invention and a trocar, preferably a bone access trocar, suitable to be positioned adjacent to an exterior surface of a targeted tissue.

According to one embodiment, the steerable device, especially the friction reduction cannula, is inserted in the trocar and connected by the locking ring. According to an alternative embodiment, the trocar is threadedly connected to the hub.

According to one embodiment, the control mechanism comprises a friction reduction cannula made from steel, preferably stainless steel.

Definitions

In the present invention, the following terms have the following meanings:

As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

The words "proximal" and "distal" refer to directions respectively towards and away from the surgeon using the medical device.

"Rod" or "Steerable rod" refers to a rod or bar comprising a part having a predefined bent or curvature.

"Secured" means attached, coupled or connected in a non-detachable manner unintentionally. Therefore, the term secured may comprise for instance the term integrally connected or over-molded.

"Tissue" refers herein to soft tissue or hard tissue. According to a preferred embodiment, tissue refers to hard tissue such as bone tissue.

DETAILED DESCRIPTION

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted.

According to a first aspect of the invention, there is provided a control mechanism for controlling a rod used for creating cavities in tissue, comprising a friction reduction cannula and a handle.

As depicted in FIG. 1, the control mechanism 100 elongates along a longitudinal axis 101 between a proximal end 100 a and a distal end 100 b spaced apart from the proximal end 100 a. The control mechanism 100 comprises a friction reduction cannula 110 and a handle 130.

As depicted in FIGS. 2, 3 and 4, the handle 130 is configured to be grasped by the user and comprises a sliding ring 131, a sliding shaft 132 and a drive shaft 133. The handle 130 extends along a longitudinal axis 101 from a proximal end to a distal end.

The sliding ring 131 is cylindrical or tubular, extends along a longitudinal axis 101 and comprises a central opening from a proximal end 131 a to a distal end 131 b. According to one embodiment, the central opening is configured to receive the sliding shaft 132 and the drive shaft 133. According to one embodiment, the sliding ring 131, especially the central opening comprises a threaded inner surface. According to one embodiment, the threaded inner surface of the sliding ring 131 is a cylindrical surface formed with a continuous thread.

The sliding shaft 132 is cylindrical or tubular, extends along a longitudinal axis 101 and comprises a central opening from a proximal end 132 a to a distal end 132 b. According to one embodiment, the central opening is configured to receive a drive shaft 133. According to one embodiment, the sliding ring 131 is cylindrical and is outside and encloses at least partially the sliding shaft 132. According to one embodiment, the sliding shaft 132 comprises at least one tab, pin or protrusion 1321 extending outwardly, preferably at the proximal end thereof 132 a. According to one embodiment, the outer surface of the sliding shaft 132 comprises marks indicating the translation of the sliding ring 131 relative to the sliding shaft 132.

The sliding ring 131 is threadedly connected to the sliding shaft 132. According to one embodiment, the protrusion(s) 1321 of the sliding shaft 132 engage or mate with threaded inner surface of the sliding ring 131. More particularly, the external protrusion(s) 1321 of the sliding shaft 132 is engaged with the internal thread of threaded inner surface of the sliding ring 131. Rotation of the sliding ring 131 causes sliding shaft 132 to move relatively along a helical path of the thread of threaded inner surface of the sliding ring 131. More particularly, rotation of the sliding ring 131 causes protrusions 1321 of the sliding shaft 132 to track the helical path of the thread of threaded inner surface of the sliding ring 131. So, rotation about the longitudinal axis of the sliding ring 131 causes the sliding shaft 132 to move back and forth along the longitudinal axis 101, relative to the sliding ring 131. With respect to the sliding shaft 132, rotation of the sliding ring 131 causes the sliding ring 131 to move back and forth along the longitudinal axis 101 in rotation.

According to an alternative embodiment wherein the sliding ring is threadedly connected to the sliding shaft; the sliding shaft 132 comprises a threaded outer surface and the sliding ring comprises an at least one tab, pin or protrusion extending inwardly, preferably at the distal end thereof and engage the threaded outer surface of the sliding shaft.

The drive shaft 133 is cylindrical or tubular, extends along a longitudinal axis 101 and comprises a central opening from a proximal end 133 a to a distal end 133 b. According to one embodiment, the sliding shaft 132 is cylindrical and is outside and encloses at least partially the drive shaft 133. According to one embodiment, the drive shaft 133 is configured to slide longitudinally inside the sliding shaft 132.

According to one embodiment, the drive shaft 133 and the sliding shaft 132 are connected by blocking means which prevent axial rotation between the drive shaft 133 and the sliding shaft 132 and which allow the drive shaft 133 to slide within the sliding shaft 132. According to one embodiment, the drive shaft 133 comprises at least one key sliding in a keyseat, such as at least one longitudinal slot, in the internal surface of the sliding shaft 132. Alternatively, the sliding shaft 132 comprises at least one key sliding in a keyseat, such as at least one longitudinal slot, in the external surface of the drive shaft 133. Consequently, the drive shaft 133 is prevented from rotating axially relative to said sliding shaft 132.

According to one embodiment, the drive shaft 133 is connected to the sliding ring 131 by means of a connecting means, such as shoulders and grooves. According to one embodiment, said connecting means form a bearing, such as a plain bearing. According to one embodiment, the bearing allows axial rotation of the sliding ring 131 relative to the drive shaft 133 about the longitudinal axis of the rod. According to one embodiment, the bearing prevents any other degrees of freedom. According to one embodiment, the drive shaft 133 is connected with the sliding ring 131 by means of a bearing which prevents axial displacement between the drive shaft 132 and the sliding ring 131 and which allows axial rotation between the drive shaft 132 and the sliding ring 131. Consequently, as the threads of the sliding ring 131 track the protrusions(s) 1321 of the sliding shaft 132, driving the sliding ring 131 into a helical path, the drive shaft 133 translates in a longitudinal axis relative to the sliding shaft 132. According to one embodiment, the drive shaft 133 and the sliding ring 131 are connected together at or near their proximal end 131 a, 133 a.

According to one embodiment, the proximal end 133 a of the drive shaft 133 comprises a connecting thread 1331, protruding proximally. In one embodiment, said connecting thread 1331 is any connecting thread known by one skilled in the art such as a "luer" type allowing connections of multiple devices equipped with mating threads.

According to one embodiment, the handle 130 comprises a connecting cap 135 comprising an inner thread so that the connecting cap 135 can be assembled onto the connecting thread 1331. According to one embodiment the connecting cap 135 comprises a plurality of flexible lugs 1351 protruding outwardly and distally. Said flexible lugs 1351 engage a plurality of openings at or near the proximal end 131 a of the sliding ring 131 thereby preventing rotation of the sliding ring. Consequently when the connecting cap 135 is assembled onto the connecting thread 1331, the sliding ring 131 cannot axially rotate about the longitudinal axis 101 relative to the sliding shaft 132. According to one embodiment, the outer surface of the connecting cap 135 comprises a thread.

According to one embodiment, the sliding shaft 132 comprises a hub 1322 extending distally and outwardly from the sliding shaft 132. According to one embodiment, the connection between the hub 1322 and the sliding shaft 132 prevents any degrees of freedom. According to one embodiment, the sliding shaft 132 and the hub 1322 are integral. According to one embodiment, the handle 130, especially the sliding shaft 132, more particularly the hub 1322, comprises arrows pointing to the same direction.

According to one embodiment, the handle 130 may be manipulated from a retracted position to a deployed position. In the retracted position, the protrusion(s) 1321 of the sliding shaft 132 engage the distal end of the thread of the sliding ring 131, as depicted in FIGS. 5, 6 and 9. In the deployed configuration, the protrusion 1321 of the sliding shaft 132 engage the proximal end of the thread of the sliding ring 131 as depicted in FIGS. 7, 8 and 9.

As depicted in FIG. 1, the friction reduction cannula 110 extends along a longitudinal axis 101. The friction reduction cannula defines a proximal end 110 a and a distal end 110 b that is spaced apart from the proximal end 110 a along the longitudinal axis. The friction reduction cannula 110 also defines an outer cannula surface and an inner cannula surface opposite the outer cannula surface. The inner cannula surface defines a cannula opening elongating along the longitudinal axis between the proximal end 110 a and the distal end 110 b.

According to one embodiment, the cross-sectional section of the inner cannula surface of the friction reduction cannula 110 is constant along the longitudinal axis. According to one embodiment, as depicted in FIGS. 10, 11 and 12; the friction reduction cannula opening is configured and sized to receive at least a portion of a rod 210. The friction reduction cannula 110 is configured to enclose at least partially a rod 210 as depicted in FIGS. 10, 11 and 12.

According to one embodiment, when used with a rod 210, the friction reduction cannula 110 is configured to restrain at least partially the rod 210 in a straight configuration along the longitudinal axis in order to ease insertion of the rod within a trocar 310, such as a bone access trocar. According to one embodiment, the friction reduction cannula 110 is configured to be used coaxially with the rod 210 for restraining at least partially the rod 210 is a straight configuration along the longitudinal axis.

According to one embodiment, the cross-sectional section of the outer cannula surface of the friction reduction cannula 110 is constant along the longitudinal axis. According to one embodiment, the friction reduction cannula opening is configured and sized to be received in at least a portion of a trocar 310, such as a bone access trocar. The trocar 310 is configured to enclose at least partially the friction reduction cannula 110 as depicted in FIG. 4.

According to one embodiment, the handle 130 further comprises locking means configured to connect a trocar 310, sized to enclose at least partially the friction reduction cannula 110, to the handle 130. As detailed hereafter, said locking means may be positioned on the hub 1322 and may be a locking ring 1323 or any connecting thread.

According to one embodiment, as depicted in FIGS. 2 and 3, the friction reduction cannula 110 is secured to drive shaft 133. According to a preferred embodiment, the proximal end of the friction reduction cannula 110 a is secured to distal end 133 b of the drive shaft 133. In one exemplary embodiment, the drive shaft 133 is molded over the friction reduction cannula 110. According to one embodiment, the friction reduction cannula 110 and the drive shaft 133 are connected by an O-ring.

According to an alternative embodiment, as depicted in FIGS. 16, 17 and 18, the friction reduction cannula 110 is secured to the sliding shaft 132, especially with the hub 1322. According to a preferred embodiment, the proximal end of the friction reduction cannula 110 a is secured to the distal end of the sliding shaft 132 b, especially with the hub 1322.

According to one embodiment, as depicted in FIG. 11, the friction reduction cannula 110 comprises a proximal part 111 and a distal part 112. According to one embodiment, the distal part 112 of the friction reduction cannula 110 is more flexible than the proximal part 111 of the friction reduction cannula 110. According to one embodiment, the proximal part 111 of the friction reduction cannula 110 is made from steel, preferably stainless steel.

According to one embodiment, the distal part of the friction reduction cannula 112 is made from polymeric material, such as polyether block amide. According to one embodiment, the ratio between the length along the longitudinal axis of the distal part 112 and the length along the longitudinal axis of the proximal part 111 is ranging from ½ to ⅙. According to one embodiment, when used with a rod having a predefined bent, the distal part of the friction reduction cannula 112 has a length equal to the length of the bent part of the rod 210.

According to one embodiment, when used with a rod 210 having a predefined bent, the proximal part of the friction reduction cannula 111 is configured to restrain the rod 210 in a straight configuration when the distal end 210 b of the rod does not extend out distally from the proximal part 111. According to one embodiment, the distal part of the friction reduction cannula 112 is not configured to restrain the rod 210 in a straight configuration when the distal end 210 b of the rod 210 extends out distally from the proximal part 111; the distal part 112 follows the curvature of the rod 210.

According to one embodiment, when the friction reduction cannula 110 is secured to the drive shaft 133, the friction reduction cannula is made of two parts: a proximal part 111 and a distal part 112 more flexible then the proximal part.

According to one embodiment, in order to avoid that the distal part 112 shrinks during insertion in the tissue, the distal part comprises metal reinforcements. According to one embodiment, the polymeric material of the distal part 112 is over-molded on the metallic reinforcements.

According to an alternative embodiment, the friction reduction cannula 110 is made in a single piece. According to said embodiment, the friction reduction cannula 111 is made from steel, preferably stainless steel.

According to one embodiment, when used with a rod 210, the friction reduction cannula 110 is configured to restrain the rod 210 in a straight configuration when the distal end of the rod 210 b does not extend out distally from the friction reduction cannula 110.

According to one embodiment, when the friction reduction cannula 110 is secured with the sliding shaft 132, the friction reduction cannula 110 is made in a single piece.

According to a second aspect of the invention, there is also provided a steerable device for creating cavities and injecting material in tissue using minimally invasive techniques.

The steerable device 200 according to the invention comprises the control mechanism 100 of the invention and a rod 210. The rod 210 passes through the drive shaft 133 and the sliding shaft 132 of the control mechanism 100.

According to one embodiment, the rod 210 has a predefined bend. According to one embodiment, only the distal part of the rod is bent, preferably from 1 to 50%, preferably from 2 to 25%, more preferably from 5 to 10% of the length of the rod 210. According to said embodiment, the proximal part of the rod 210 extends along a longitudinal axis 101. The rod 210 defines a proximal end 210 a and a distal end 210 b that is spaced apart from the proximal end 210 a According to one embodiment, the angle of deflection of the rod 210 ranges from 20° to 150°, preferably from 30° to 130°, more preferably from 40° to 110° (as measured from the longitudinal axis). According to one embodiment, the cross-sectional section of the rod 210 is constant. According to one embodiment, the rod 210 has no opening along its length.

According to one embodiment, the length of the rod 210 along the longitudinal axis 110 is equal to the length along the longitudinal axis 110 from the proximal end of the handle 130 to the distal end of the friction reduction cannula 110 b.

According to one embodiment, the rod 210 comprises a superelastic material, preferably an alloy of nickel and titanium.

According to one embodiment, the rod 210 comprises a knob 211 at its proximal end 210 a. According to one embodiment, the knob 211 is free in rotation relative to the rod 210. According to one embodiment, the rod 210 is connected to the knob 211 by means of a bearing, such as a plain bearing. According to one embodiment, the bearing allows axial rotation of the knob 211 relative to the rod 210 about the longitudinal axis of the rod. According to one embodiment, the knob 211 comprises a threaded inner surface suitable for mating the thread of the connecting cap 135. Due to the bearing, the knob 211 of the rod 210 may be screw on the connecting cap 135 without axial rotation of the rod 210. According to one embodiment, the knob 211 further comprises at the distal end of the threaded inner surface a protrusion, such as a sawtooth protrusion, or a recess to be engaged in respectively a recess or a protrusion 1352 within the connecting cap 135. Thus, once the knob 211 has been screwed onto the connecting cap 135 so that the protrusion 1352 engages the recess, the knob 211 and the connecting cap 135 do not rotate independently. Thus unscrewing of the knob 211 disengages the connecting cap 135 from the connecting thread 1331.

According to one embodiment, once the protrusion 1352 of the connecting cap engages a recess of the knob 211, the threaded inner surface of the knob 211 depresses the flexible lugs 1351 inside the central opening of the sliding ring, so that the sliding ring 131 may be rotated relative to the drive shaft 133. Consequently, when the knob 211 of the rod 210 has been screwed onto the connecting cap 135, the sliding ring 131 can axially rotate about the longitudinal axis 101 relative to the sliding shaft 132.

According to one embodiment, the deflection plane of the rod 210 may be pre-determined. According to one embodiment, the rod 210 comprises, preferably proximally, at least one key sliding in a keyseat, such as at least one longitudinal slot, in the internal surface of the drive shaft 133. Consequently, the rod 210 is prevented from rotating axially relative to said drive shaft 133. Due to said key of the rod 210, the deflection plane of the rod 210 may be predefined relative to the drive shaft 133. According to one embodiment, as the drive shaft 133 is prevented from axially rotating relative to the sliding shaft 132, the deflection plane of the rod 210 is also predefined relative to the sliding shaft 132 and thus relative to the hub 1322 of the handle; so that the arrows of the hub 1322 point towards the direction of the preformed bent of the rod 210.

According to a further aspect of the invention, there is provided a steerable system 300 for creating cavities and injecting material in tissue using minimally invasive techniques.

The steerable system 300 according to the invention comprises the steerable device of the invention and a trocar 310, such as a bone access trocar.

According to one embodiment, the trocar 310 extends along a longitudinal axis 101 from a proximal end 310 a to a distal end 310 b spaced apart from the proximal end 310 a along the longitudinal axis 101. According to one embodiment, the length of the trocar 310 along the longitudinal axis 101 is equal to the length along the longitudinal axis 101 of the friction reduction cannula 110 from the hub 1322 to the distal end of the friction reduction cannula 110 b.

The trocar 310 also defines an outer trocar surface and an inner trocar surface opposite the outer trocar surface. The inner trocar surface defines a trocar opening elongating along the longitudinal axis 101 between the distal end 310 b and the proximal end 310 a. According to one embodiment, the trocar opening is configured and sized to receive at least a portion of the steerable device according to the invention, especially at least a portion of the friction reduction cannula 110. According to one embodiment, the cross-sectional section of the inner surface of the trocar 310 is constant along the longitudinal axis 101.

According to one embodiment, the trocar 310 is connected to the distal end of the handle 130, preferably to the distal end of the sliding shaft 132 b, more preferably to the hub 1322. According to one embodiment, the control mechanism 100, especially the friction reduction cannula 110, is inserted in the trocar 310 and the trocar 310 is connected to the distal end of the handle 130, preferably to the distal end of the sliding shaft 132 b, more preferably to the hub 1322, by a locking ring 1323. According to one embodiment, the trocar 310 comprises a connecting thread 311 at its proximal end 310 a. The said connecting thread 311 is any connecting thread known by one skilled in the art such as a "luer" type allowing connections of multiple devices equipped with mating threads According to said embodiment, the trocar 310, especially the connecting thread 311, is threadedly connected to the distal end of the handle 130, preferably to the distal end of the sliding shaft 132 b, more preferably to the hub 1322, in a detachable manner.

According to one embodiment, the hub 1322 comprises a locking ring 1323 for locking the trocar 310 onto the handle 130. According to one embodiment, the mating surfaces between the sliding shaft 132 and the trocar 310 guarantee that the control mechanism 100 is properly located onto the trocar 310 both in longitudinal translation and in axial rotation about the longitudinal axis. According to one embodiment, when the locking ring 1323 is actuated, there is no degree of freedom between the handle 130 and the trocar 310; the trocar 130 is secured to the hub 1322.

According to one embodiment (as explained hereabove), when the friction reduction cannula 110 is made in a single piece, the friction reduction cannula 110 is secured to the sliding shaft 132.

In use, the rod 210 is inserted within the control mechanism 100 with the handle 130 is in the retracted position. The knob 211 of the rod 210 is screwed onto the connecting cap 135. In this position, the rod 210 is in a straight configuration. The control mechanism 100 comprising the rod 210 in its retracted position may then be slid through the trocar 310 which has been placed in an appropriate location in the patient's tissue. The rod may then be deployed by rotating the sliding ring in the deployed configuration. In the deployed configuration, the rod 210 extends laterally outside of the friction reduction cannula 110 and of the trocar 310. Said steps may be repeated with different direction of the deflection plane, in order to create multiple interdigitated cavities. Once the cavities have been created, the rod 210 may be removed by unscrewing the knob 211 and thus allowing access to the connecting thread 1331 (the connecting cap 135 being removed with the knob 211). An injection device 320 may then be connected to the connecting thread 1331 in order to inject material within the created cavities through the drive shaft 133 and the friction reduction cannula 110.

According to one embodiment (as explained hereabove), when the friction reduction cannula 110 is made in two parts, the friction reduction cannula 110 is secured with the drive shaft 133.

When the friction reduction cannula 110 comprises a proximal part 111 and a distal part 112, the steerable device 110 needs to be armed in order to bring the distal end of the rod 210 b from a retracted position inside the proximal part of the friction reduction cannula 111, as depicted in FIG. 10, to an operational position at the distal end of the distal part of the friction reduction cannula 112, as depicted in FIGS. 5 and 6.

To this end, once the control mechanism 100 comprising the rod 210 is slid through the trocar 310 which has been placed in an appropriate location in the patient's tissue and then locked onto the trocar 310, the rod 210 is pushed until the knob 211 comes in contact with the connecting cap 135. The knob 211 is then screwed on the connecting cap 135. As explained hereabove, fully screwing knob 211 onto the connecting cap 135, protrusion or recess of the knob 211 engages respectively a recess or protrusion 1352 of the connecting cap 135, thus locking the knob 211 on the connecting cap 135. Fully screwing knob 211 onto the connecting cap 135 also pushes inwards the flexible lugs 1351, freeing them from the corresponding openings in the proximal end of the sliding ring 131 a, thus allowing rotation of the sliding ring 131.

According to one embodiment, when the distal end of the threaded inner surface of the sliding ring 131 engages with the protrusion(s) 1321 of the sliding shaft 132 (retracted position), and when the steerable device is secured to the trocar 310, the translation of the drive shaft to the deployed position caused by the rotation of the sliding ring 131 drives both the friction reduction cannula 110 and the rod 210 to extends out of the trocar laterally, thus creating a cured cavity in the tissue, as depicted in FIGS. 7 and 8.

Once the cavity has been created, the rod 210 may be removed by unscrewing the knob 211 and thus allowing access to the connecting thread 1331 (the connecting cap 135 being removed with the knob 211). An injection device may then be connected to the connecting thread 1331 in order to inject material within the created cavities through the drive shaft 133 and the friction reduction cannula 110, as depicted in FIGS. 13, 14 and 15. Due to the flexible part of the friction reduction cannula 112 and by rotating the handle from the deployed position to the retracted position, material may be injected in a retrograde manner.

According to one embodiment, the material may be any material known to one skilled in the art, such as bone cement.

While various embodiments have been described and illustrated, the detailed description is not to be construed as being limited hereto. Various modifications can be made to the embodiments by those skilled in the art without departing from the true spirit and scope of the disclosure as defined by the claims.

BRIEF DESCRIPTION OF THE DRAWINGS

As explained in the specification hereabove, FIGS. 1 to 15 relate to a control mechanism, a steerable device and a steerable system wherein the friction reduction cannula comprises a distal part and a proximal part and is connected to the drive shaft. FIGS. 16 to 18 relate to a control mechanism, a steerable device and a steerable system wherein the friction reduction cannula is made of a single piece and is connected to the sliding shaft.

FIG. 16 is a front view of the steerable system with the control mechanism in the retracted position according to one embodiment of the invention, without the rod.

FIG. 17 is a sectional view of the steerable system of FIG. 16 along plane AA.

FIG. 18 is a sectional view of FIG. 16 along plane BB.

REFERENCES

Figure 1:
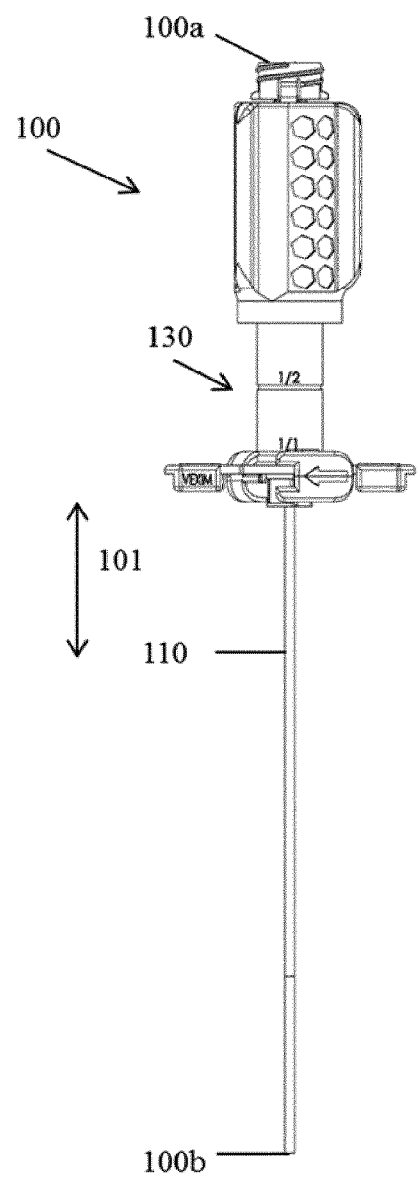
FIG. 1 is a front view of the control mechanism according to one embodiment of the invention.
Figure 2:
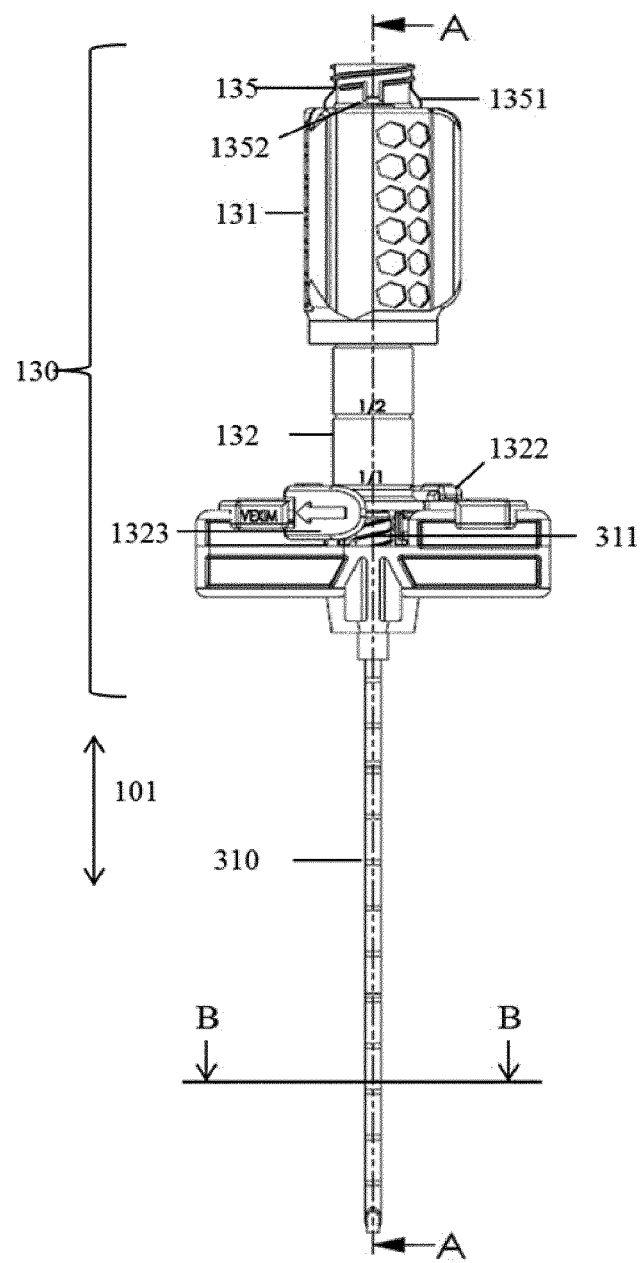
FIG. 2 is a front view of the steerable system with the control mechanism in the retracted position according to one embodiment of the invention, without the rod.
Figure 3:
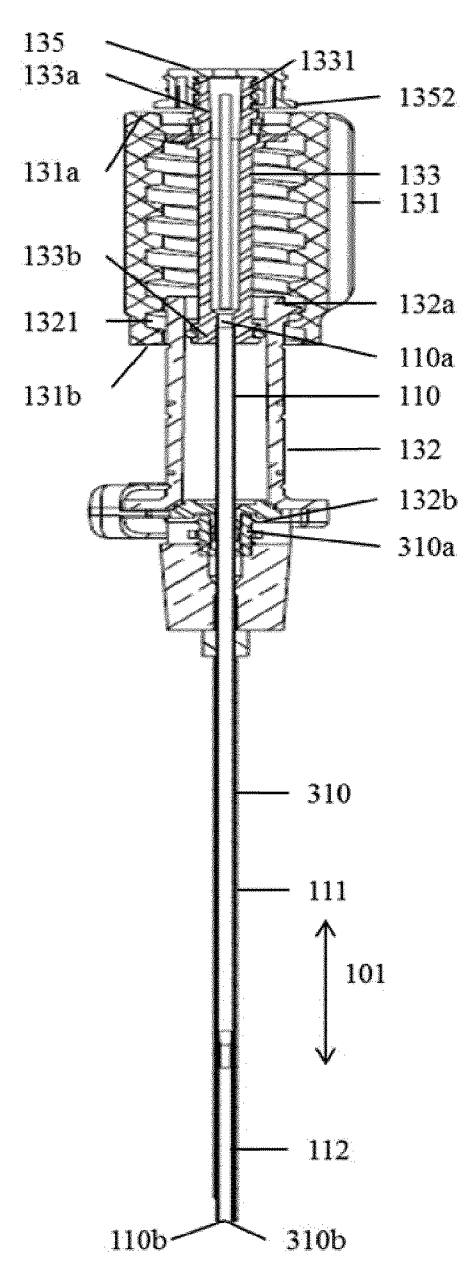
FIG. 3 is a sectional view of the steerable system of FIG. 2 along plane AA.
Figure 4:
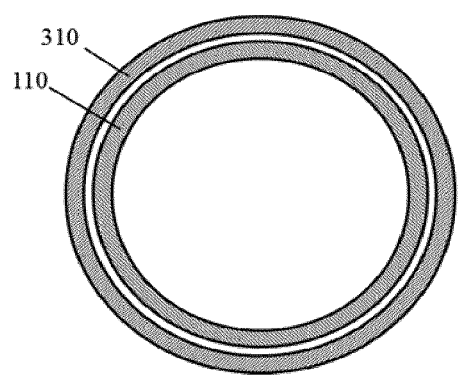
FIG. 4 is a sectional view of FIG. 2 along plane BB.
Figure 5:
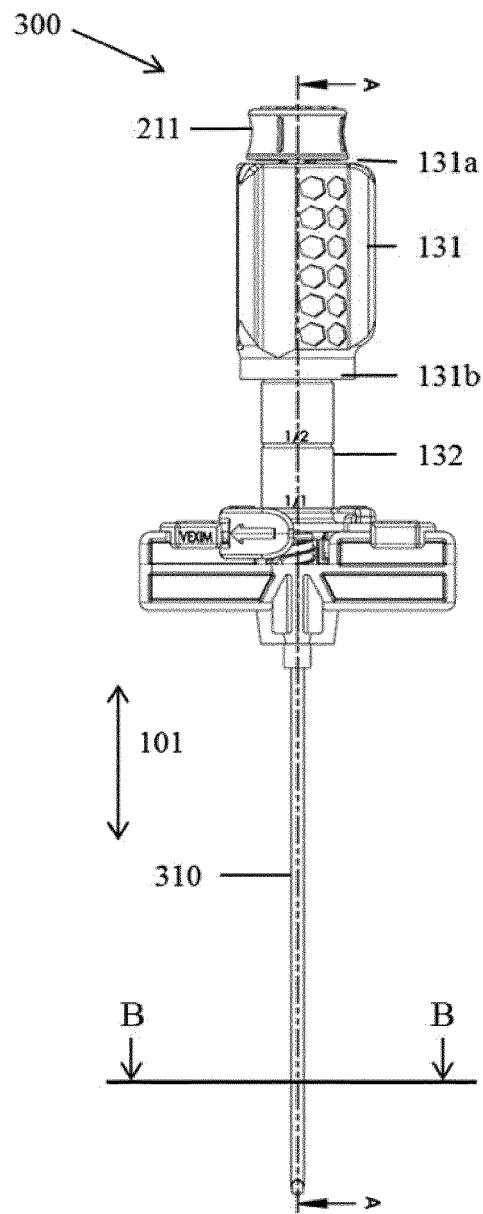
FIG. 5 is a front view of the steerable system with the control mechanism in the armed position according to one embodiment of the invention.
Figure 6:
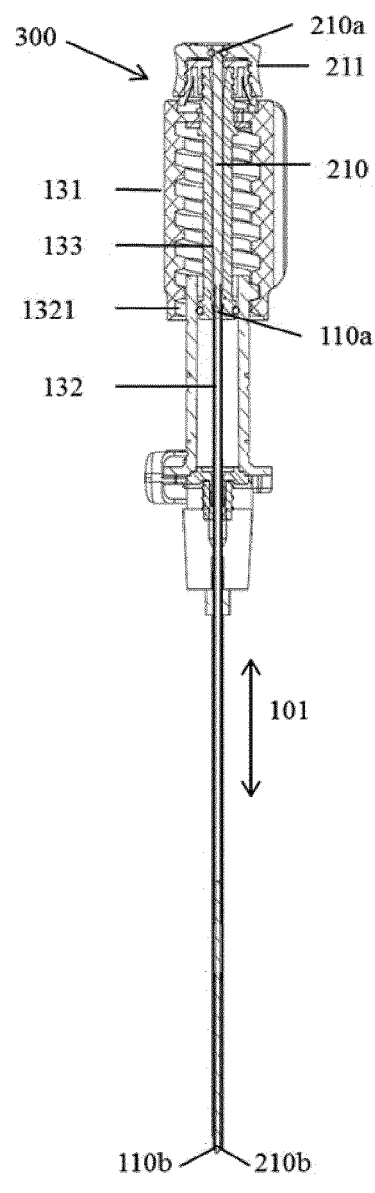
FIG. 6 is a sectional view of the steerable system of FIG. 5 along plane AA.
Figure 7:
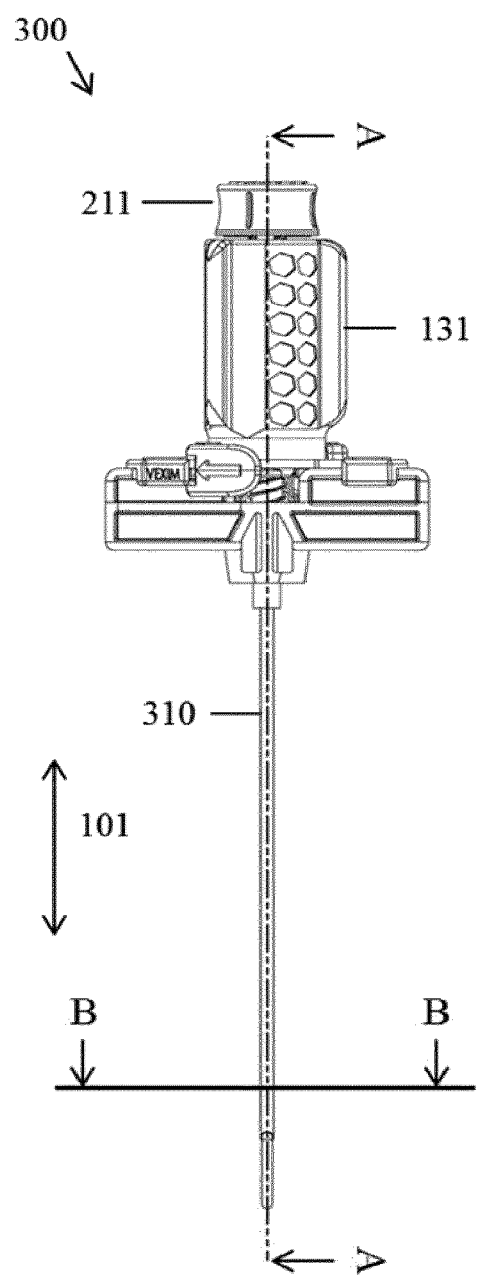
FIG. 7 is a front view of the steerable system with the control mechanism in the deployed position according to one embodiment of the invention.
Figure 8:
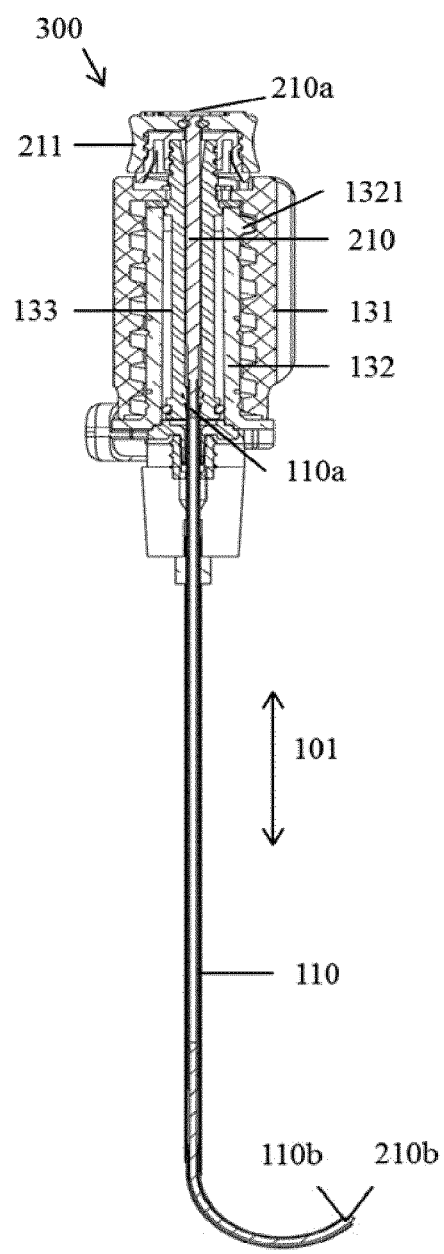
FIG. 8 is a sectional view of the steerable system of FIG. 7 along plane AA.
Figure 9:
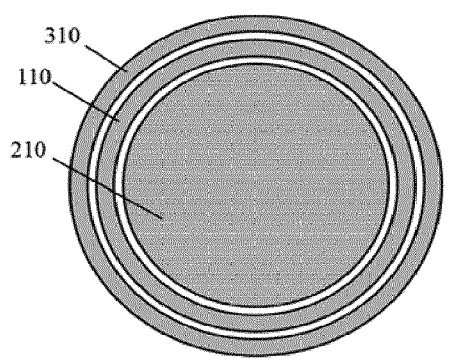
FIG. 9 is a sectional view of the steerable system of FIGS. 5 and 7 along plane BB.
Figure 10:
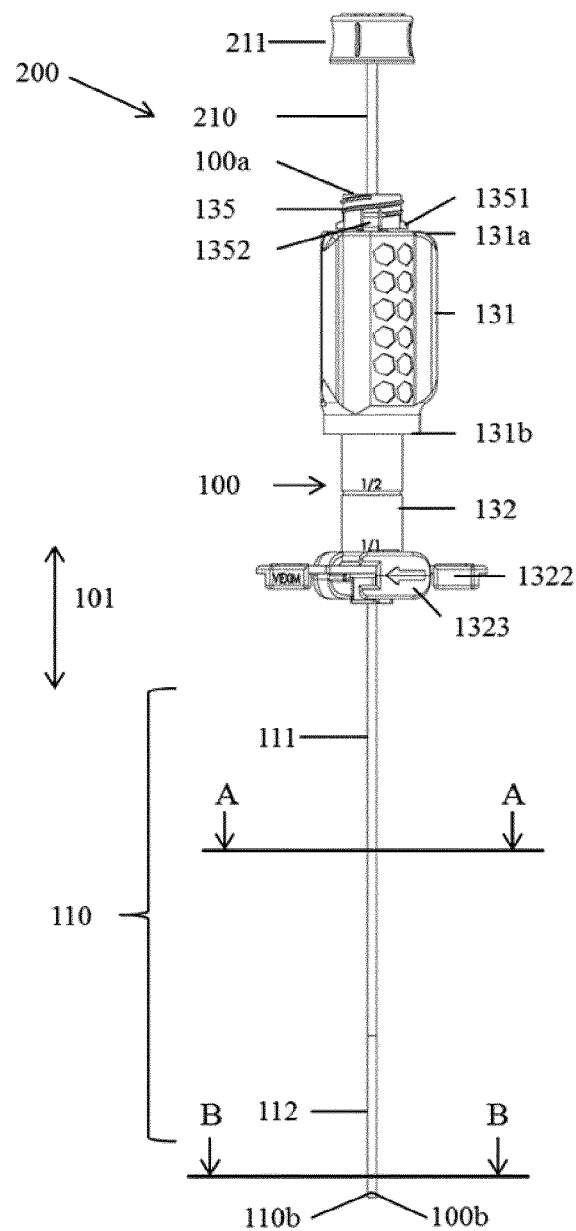
FIG. 10 is a front view of the steerable device in the retracted position according to one embodiment of the invention.
Figure 11:
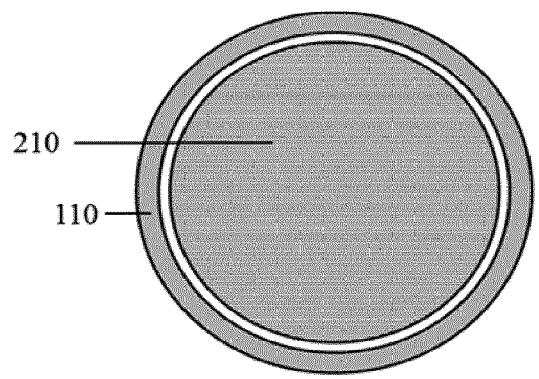
FIG. 11 is a sectional view of the steerable device according to FIG. 10 along plane AA.
Figure 12:
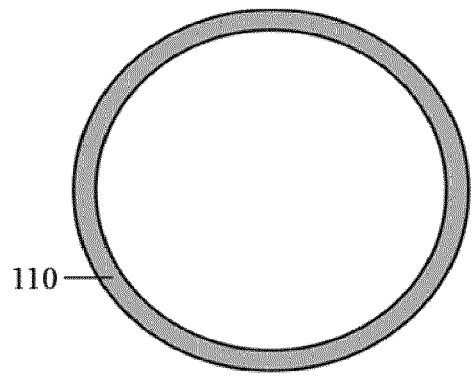
FIG. 12 is a sectional view of the steerable device of FIG. 10 along plane BB.
Figure 13:
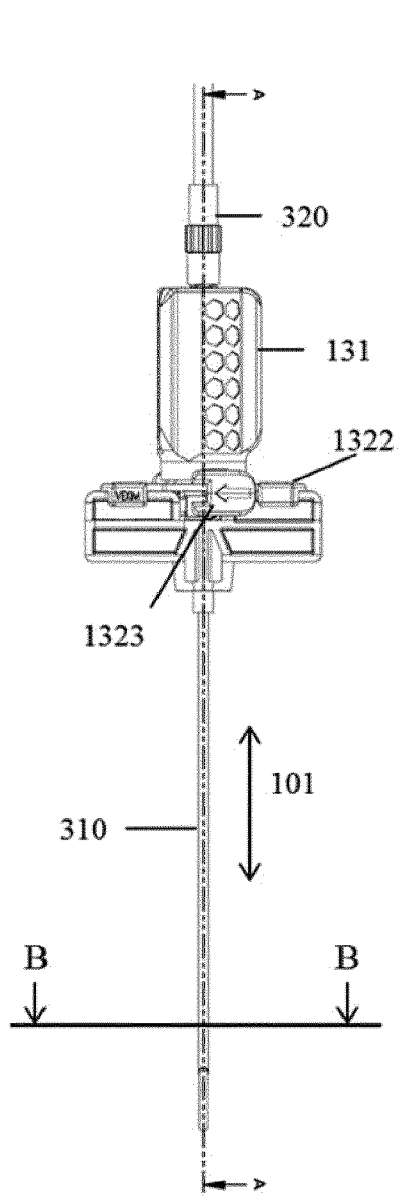
FIG. 13 is a front view of the steerable system with the control mechanism connected with an injection device.
Figure 14:
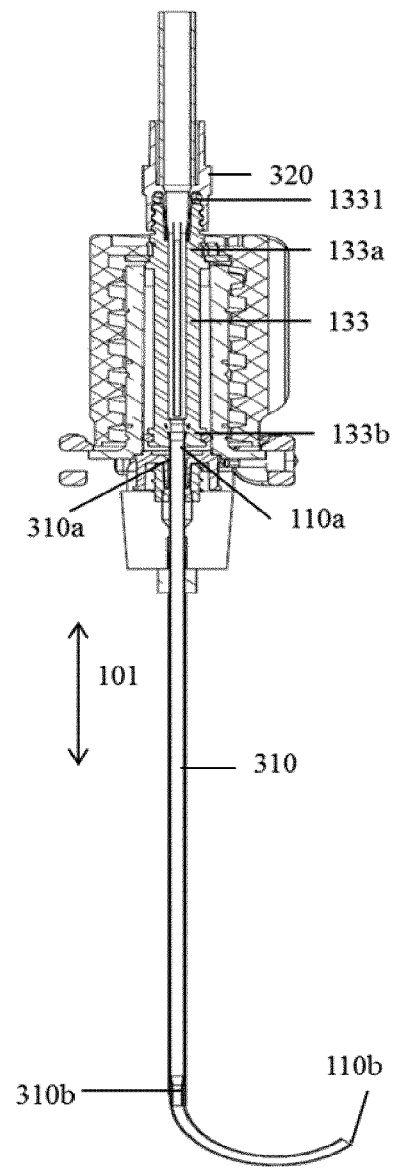
FIG. 14 is a sectional view of the steerable system of FIG. 13 along plane AA.
Figure 15:
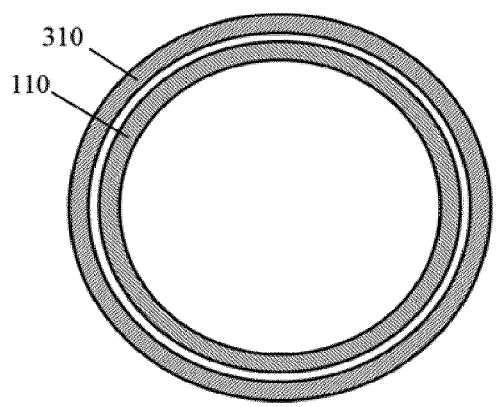
FIG. 15 is a sectional view of FIG. 13 along plane BB.
Figure 18:
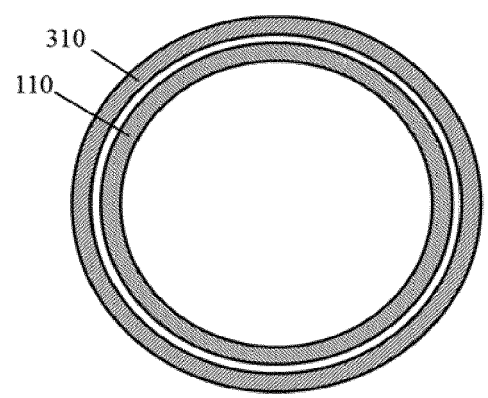

100—Control mechanism;
100 a—Proximal end of the control mechanism;
100 b—Distal end of the control mechanism;
101—Longitudinal axis of the control mechanism;
110—Friction reduction cannula;
110 a—Proximal end of the friction reduction cannula;
110 b—Distal end of the friction reduction cannula;
111—Proximal part of the friction reduction cannula;
112—Distal part of the friction reduction cannula;
130—Handle;
131—Sliding ring;
131 a—Proximal end of the sliding ring;
131 b—Distal end of the sliding ring;
132—Sliding shaft;
132 a—Proximal end of the sliding shaft;
132 b—Distal end of the sliding shaft;
1321—Protrusion of the sliding shaft;
1322—Hub;
1323—Locking ring;
133—Drive shaft;
133 a—Proximal end of the drive shaft;
133 b—Distal end of the drive shaft;
1331—Connecting thread;
135—Connecting cap;
1351—Flexible lug;
1352—Protrusion;
200—Steerable device;
210—Rod;
210 a—Proximal end of the rod;
210 b—Distal end of the rod;
211—Knob of the rod;
300—Steerable system;
310—Trocar;
310 a—Proximal end of the trocar;
310 b—Distal end of the trocar;
311—Connecting thread;
320—Injection device.

What is claimed is:

1. A steerable system for accessing bone, said steerable system comprising:
a trocar extending along a longitudinal axis from a proximal end to a distal end spaced apart from said proximal end;
a control mechanism comprising:
a handle configured to be detachably secured to said trocar, said handle comprising a sliding shaft, and a drive shaft coupled to said sliding shaft such that rotation of said drive shaft relative to said sliding shaft about the longitudinal axis is prevented and translation of said drive shaft relative to said sliding shaft along the longitudinal axis is permitted;
a cannula coupled to said sliding shaft or said drive shaft; and
a rod comprising a preformed bend, said rod removably disposed within said cannula, wherein said rod is prevented from rotating relative to said drive shaft about the longitudinal axis such that a deflection plane of said preformed bend is predefined relative to each of said sliding shaft, said handle, and said trocar when said handle is coupled to said trocar.

2. The steerable system of claim 1, wherein said control mechanism further comprises a hub extending outwardly from said sliding shaft, and a locking ring coupled to said hub for selectively locking said hub with said trocar.

3. The steerable system of claim 2, further comprising an arrow disposed on said hub with said arrow being indicative of said deflection plane of said preformed bend of said rod.

4. The steerable system of claim 1, wherein said control mechanism further comprises a sliding ring threadably coupled to said sliding shaft, and a bearing coupling said drive shaft and said sliding ring.

5. The steerable system of claim 1, wherein one of said drive shaft and said sliding shaft comprises at least one keyseat and the other one of said drive shaft and said sliding shaft comprises a key configured to slidably move within said at least one keyseat.

6. The steerable system of claim 1, wherein a length of said rod along the longitudinal axis is equal to a length from a proximal end of said handle to a distal end of said cannula.

7. The steerable system of claim 1, wherein said control mechanism further comprises a knob rotatably coupled to said rod and threadably coupled to said handle.

8. The steerable system of claim 7, wherein said control mechanism further comprises a connecting cap coupled to said handle, said connecting cap comprising flexible lugs engaging openings of said handle to prevent rotation of said handle relative to said drive shaft, wherein said knob is configured to depress said flexible lugs to disengage said openings and permit rotation of said handle relative to said drive shaft.

9. The steerable system of claim 1, wherein said cannula comprises a proximal part and a distal part with said distal part being more flexible than said proximal part.

10. The steerable system of claim 9, wherein said proximal part is formed from metal and said distal part is formed from polymeric material.

11. A method of accessing bone with a steerable system including a trocar and a control mechanism, wherein the control mechanism includes a handle, a cannula, and a rod disposed within the cannula and having a preformed bend, said method comprising:
   positioning a distal end of the trocar within the bone;
   positioning the cannula and the rod within the trocar, wherein the preformed bend of the rod is restrained to a straight configuration;
   securing the handle to the trocar;
   coupling the rod to a drive shaft of the handle; and
   rotating a sliding ring of the handle about a longitudinal axis of the trocar to translate the drive shaft along the longitudinal axis relative to a sliding shaft of the handle, wherein translation of the drive shaft advances the rod beyond the distal end of the trocar such that the preformed bend extends laterally out of the trocar in a deflection plane that is predefined relative to the trocar.

12. The method of claim 11, wherein the sliding ring is initially rotationally fixed relative to the drive shaft, said method further comprising coupling a knob to the handle to disengage the sliding ring from the drive shaft, thereby permitting rotation of the sliding ring relative to the drive shaft.

13. The method of claim 12, further comprising:
   decoupling the knob from the handle after the step of rotating the sliding ring of the handle; and
   removing the rod from the cannula.

14. The method of claim 13, wherein the step of coupling the knob to the handle further comprises coupling the knob to a connecting cap threadably coupled to the handle such that the knob and the connecting cap do not rotate independently, said method further comprising decoupling the connecting cap from the handle with rotation of the knob.

15. The method of claim 14, wherein the step of decoupling the connecting cap exposes a connecting thread, said method further comprising:
   coupling an injection device to the connecting thread; and
   injecting material through the cannula.

16. The method of claim 15, further comprising rotating the sliding ring of the handle about the longitudinal axis while injecting the material to inject the material in a retrograde manner.

17. The method of claim 11, wherein the step of securing the handle relative to the trocar further comprises actuating a locking ring to lock a hub of the handle to the trocar.

18. The method of claim 17, further comprising viewing an arrow on the hub of the handle to determine the deflection plane.

19. A method of accessing bone with a steerable system including a trocar and a control mechanism, wherein the control mechanism includes a handle, a cannula, and a rod disposed within the cannula and having a preformed bend, said method comprising:
   positioning a distal end of the trocar within the bone;
   positioning the cannula and the rod within the trocar, wherein the rod is restrained to a straight configuration;
   securing the handle relative to the trocar;
   rotating the handle about a longitudinal axis of the trocar in a first direction to advance the rod and the cannula beyond the distal end of the trocar, wherein the preformed bend extends laterally out of the trocar in a deflection plane that is predefined relative to the trocar;
   removing the rod from within the cannula; and
   injecting material through the cannula.

20. The method of claim 19, further comprising rotating the handle about the longitudinal axis in a second direction opposite the first direction while injecting the material to inject the material in a retrograde manner.

* * * * *